US 12,188,465 B2

(12) United States Patent
Sonoda et al.

(10) Patent No.: US 12,188,465 B2
(45) Date of Patent: *Jan. 7, 2025

(54) TUBE PUMP HOLDER WITH FIRST AND SECOND ENGAGEMENT PORTIONS

(71) Applicant: NIPRO CORPORATION, Osaka (JP)

(72) Inventors: Yoshiyuki Sonoda, Osaka (JP); Kohzo Ishikura, Osaka (JP); Takeshi Yamaguchi, Osaka (JP)

(73) Assignee: NIPRO CORPORATION, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/504,990

(22) Filed: Nov. 8, 2023

(65) Prior Publication Data

US 2024/0068464 A1  Feb. 29, 2024

Related U.S. Application Data

(62) Division of application No. 16/650,586, filed as application No. PCT/JP2018/034972 on Sep. 21, 2018, now Pat. No. 11,852,129.

(30) Foreign Application Priority Data

Sep. 26, 2017 (JP) ................................. 2017-185302

(51) Int. Cl.
F04B 43/12 (2006.01)
A61M 60/279 (2021.01)
(Continued)

(52) U.S. Cl.
CPC ....... *F04B 43/1253* (2013.01); *A61M 60/279* (2021.01); *A61M 60/113* (2021.01); *A61M 60/37* (2021.01)

(58) Field of Classification Search
CPC ........................ F04B 43/1253; A61M 60/279
See application file for complete search history.

(56) References Cited

U.S. PATENT DOCUMENTS 5,222,880 A * 6/1993 Montoya ............. F04B 43/1215
138/119
5,533,877 A * 7/1996 Friedmann ........... A61M 60/113
417/477.1

(Continued)

FOREIGN PATENT DOCUMENTS

WO    WO-2010092729 A1 * 8/2010 ............. A61M 1/14

*Primary Examiner* — Nathan C Zollinger
(74) *Attorney, Agent, or Firm* — Alleman Hall & Tuttle LLP

(57) ABSTRACT

Provided is a tube set which is capable of easily determining whether a holder has been mounted when the holder is mounted on a housing. The tube set, which is provided in a tube pump that feeds a liquid, includes a pump tube and a holder. The holder has a flexible flat plate and includes first and second engagement portions located away from each other in a first direction. The first and second engagement portions are configured to be fitted into first and second engagement grooves formed in the housing, respectively, when the holder is pushed into the housing in a state of being bent in a thickness direction. The holder is elastically restored to be attached to the housing when the engagement portions are fitted into the respective engagement grooves. The holder has a flexural modulus of 500 MPa or more and 3500 MPa or less.

6 Claims, 11 Drawing Sheets

(51) Int. Cl.
*A61M 60/113* (2021.01)
*A61M 60/37* (2021.01)

(56) References Cited

U.S. PATENT DOCUMENTS

| | | | | |
|---|---|---|---|---|
| 6,406,267 | B1 * | 6/2002 | Mondiere | F04B 43/0072 |
| | | | | 417/53 |
| 7,704,057 | B2 * | 4/2010 | Malbec | F04B 43/1284 |
| | | | | 417/474 |
| 11,852,129 | B2 * | 12/2023 | Sonoda | F04B 43/1253 |
| 2005/0254978 | A1 * | 11/2005 | Huber | F04B 43/1284 |
| | | | | 417/474 |
| 2011/0165005 | A1 * | 7/2011 | Maitre | F04B 43/1276 |
| | | | | 418/45 |
| 2020/0147281 | A1 * | 5/2020 | Delnevo | A61M 60/109 |

* cited by examiner

TUBE PUMP HOLDER WITH FIRST AND SECOND ENGAGEMENT PORTIONS

CROSS-REFERENCE TO RELATED APPLICATION

The present application is a divisional of U.S. patent application Ser. No. 16/650,586, filed Mar. 25, 2020, and entitled TUBE SET AND TUBE PUMP PROVIDED WITH SAME, which is a national phase of International Application No. PCT/JP2018/034972, filed Sep. 21, 2018, which claims priority to Japanese Patent Application No. 2017-185302, filed on Sep. 26, 2017, the entire disclosures of which are hereby incorporated herein by reference for all purposes.

TECHNICAL FIELD

The present invention relates to a tube set of a tube pump that feeds a liquid, and a tube pump including the tube set.

BACKGROUND ART

In the dialysis treatment, a dialysis device is used to remove waste and unnecessary water in the blood, and the dialysis device is provided with a tube pump for feeding a liquid such as blood and a drug solution. As a tube pump, for example, a tube pump disclosed in PTL 1 is known. The tube pump of PTL 1 includes a housing, a rotor, a tube, and an adapter component. The housing has a pump head formed therein, and the pump head has an opening at a side in front view. In the pump head, a tube is disposed along the pump head, and a rotor is disposed inside the tube. The rotor is configured to be rotatable, and rotates so as to squeeze the tube and feed the liquid in the tube. On the other hand, an adapter component is attached to both ends of the tube, and the tube is connected to the supply tube and the discharge tube of the blood circuit via the adapter component.

The adapter component thus configured can be fitted into the opening of the housing from the front to fix itself to the opening of the housing. More specifically, the adapter component has two recesses to be fixed to the housing, and the housing has clip receivers corresponding to the respective recesses. When the adapter component is fitted into the opening of the housing from the front, the clip receiver fits into the recess, and the adapter member is fixed to the housing by fitting. In this way, by fixing the adapter component to the opening of the housing, the tube can be fixed and held in the housing via the adapter component.

CITATION LIST

Patent Literature

PTL 1: JP 2007-537390 A

SUMMARY OF INVENTION

Technical Problem

In the tube pump of PTL 1, the tube can be fixed by fitting the adapter member into the housing as described above. Further, the tube needs to be replaced each time it is used, and the tube needs to be configured to be detachable from the housing. The tube forms a blood circuit together with the supply tube and the discharge tube, and is attached to the supply tube and the discharge tube via the adapter member before being attached to the housing. Therefore, when replacing the tube, it is necessary to replace the entire blood circuit. In the tube of PTL 1 configured as described above, it is required that the adapter member be easily fitted to the housing in order to facilitate replacement of the blood circuit. From such a viewpoint, a flexible material is used for the adapter member of the tube pump of PTL 1.

However, if the flexible material is used, it is difficult to obtain a feeling of mounting (for example, a feeling of clicking) when fitting the adapter member into the housing, that is, at the time of mounting, and it is difficult for a practitioner to determine whether the adapter member is properly fitted to the housing. Therefore, there is a possibility that treatment starts without the adapter member being sufficiently fitted and fixed in the housing, and a malfunction may occur, such as detachment of the adapter member from the housing during the treatment.

Therefore, an object of the present invention is to provide a tube set capable of easily determining whether a holder corresponding to an adapter member has been attached to a housing.

Solution to Problem

A tube set provided in a tube pump that feeds a liquid includes a pump tube that is curvedly disposed in a housing along an inner peripheral face of the housing, the pump tube being squeezed by a rotor disposed in the housing to pump a liquid in the pump tube, and a holder to which both ends of the pump tube are connected, and which is fixed to the housing so as to attach the pump tube to the housing. The holder has a flexible flat plate and includes a first engagement portion and a second engagement portion that are located away from each other in a first direction. The first engagement portion and the second engagement portion are configured to be fitted into a first engagement groove and a second engagement groove formed in the housing, respectively, when the holder is pushed into the housing in a state of being bent in a thickness direction. The holder is elastically restored to be attached to the housing when the first engagement portion and the second engagement portion are fitted into the first engagement groove and the second engagement groove, respectively. The holder has a flexural modulus of 500 MPa or more and 3500 MPa or less.

According to the present invention, it is possible to generate an impact sound (that is, a click sound) generated when the holder elastically returns when the engagement portion of the holder is fitted into the engagement groove, and hits the face that regulates the first engagement groove, and thereby, an impact transmitted to the finger through the impact sound. Thereby, it is possible to generate a click feeling when attaching the holder to the housing. This makes it easy to determine whether the holder has been mounted when the holder is mounted on the housing.

Advantageous Effect of Invention

The present invention makes it easy to determine whether the holder has been mounted when the holder is mounted on the housing.

DESCRIPTION OF EMBODIMENT

First Embodiment

Hereinafter, a tube pump 1 according to an embodiment of the present invention will be described with reference to the drawings. The concept of the direction used in the following description is used for convenience in the description, and does not limit the direction of the configuration of the invention to the direction. The tube pump 1 described below is merely an embodiment of the present invention. Therefore, the present invention is not limited to the embodiment, and can be added, deleted, or changed without departing from the spirit of the invention.

Figure 1:
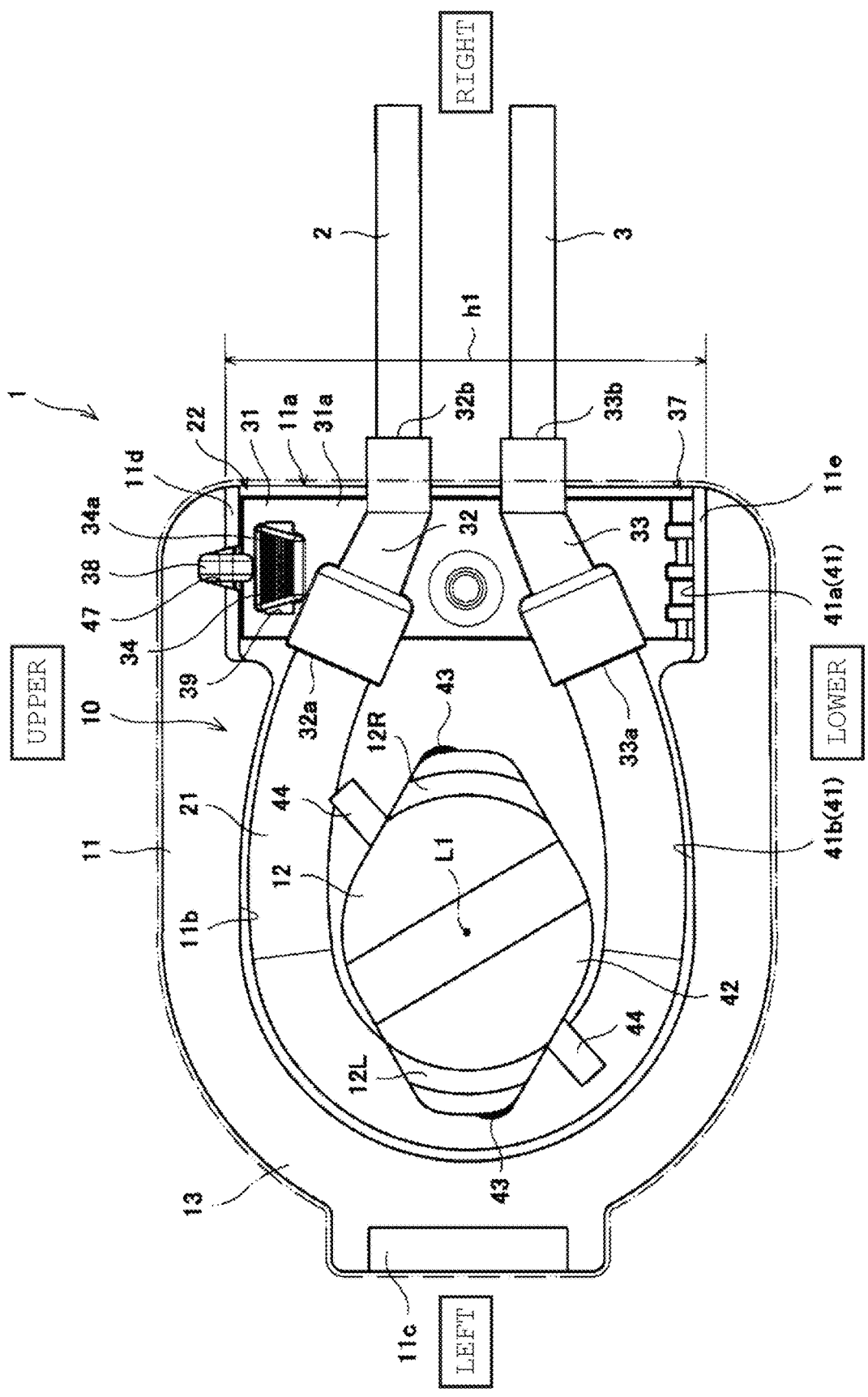
FIG. 1 is a front view of a tube pump according to a first embodiment of the present invention as viewed from the front.

The tube pump 1 shown in FIG. 1 mainly feeds a liquid such as blood or a drug solution, and is provided in, for example, a dialysis device (not shown) for performing dialysis treatment. The dialysis device is an example of a device to which the tube pump 1 is applied, and the device to which the tube pump 1 is applied is not limited to the dialysis device. That is, the tube pump 1 may be applied to a multipurpose blood processing device used for continuous slow blood purification, plasma exchange, plasma adsorption, ascites filtration concentration, and the like. A dialysis device as an example includes a blood circuit. The blood circuit draws blood from the arteries and allows blood to flow, and returns the blood to the vein after removing waste and unnecessary water in the blood. The blood circuit having such a role includes a supply tube 2 and a discharge tube 3, and these two tubes 2 and 3 are connected to the tube pump 1. Blood taken out from a blood vessel flows into the supply tube 2, and this blood is fed out to the discharge tube 3 by the tube pump 1 and returned to a vein. The tube pump 1 having such a function includes a tube set 10, a housing 11, a rotor 12, and a cover 13.

Figure 2:
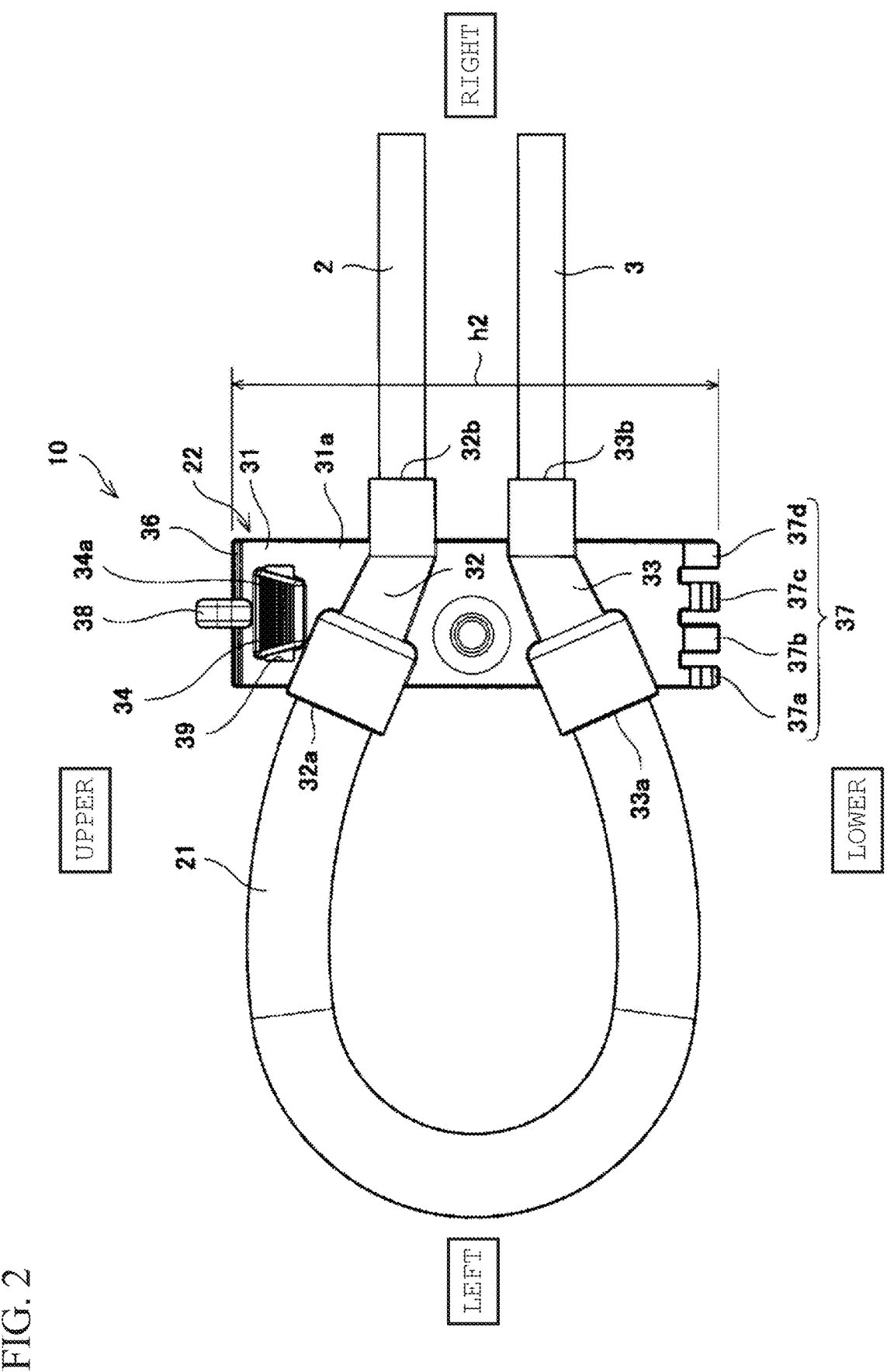
FIG. 2 is a front view of a tube set provided in the tube pump of FIG. 1 as viewed from the front.

The tube set 10 shown in FIG. 2 constitutes a blood circuit together with the supply tube 2 and the discharge tube 3, and has a pump tube 21 and a holder 22. The pump tube 21 is a long cylindrical member made of, for example, PVC (polyvinyl chloride), through which a liquid can flow. Further, the pump tube 21 has flexibility, and is configured to be bent substantially in a C shape as shown in FIG. 2 without breaking. Further, the pump tube 21 is attached to the holder 22 in a curved state.

Figure 3:
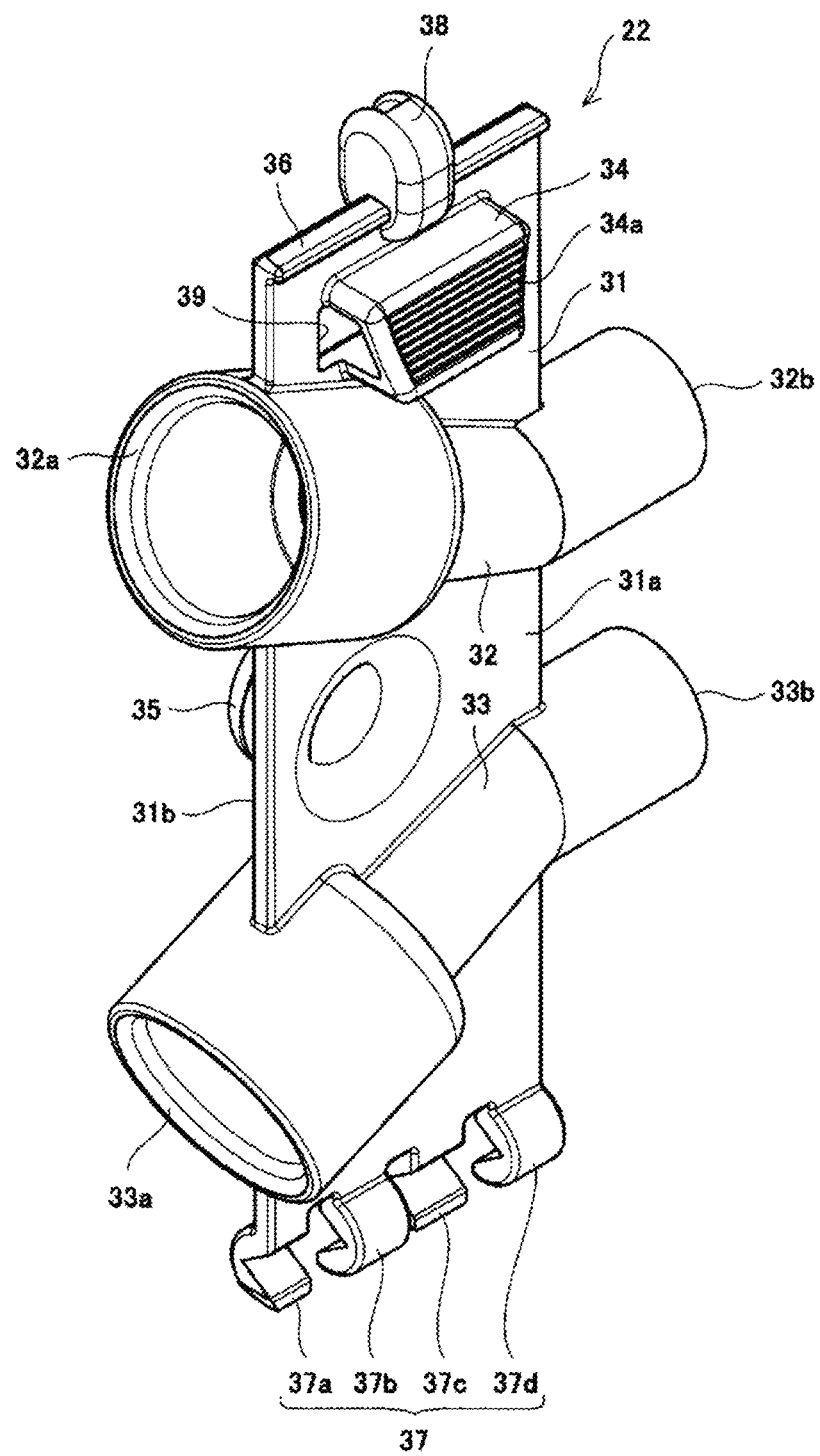
FIG. 3 is a perspective view of a holder provided in the tube set of FIG. 1 as viewed obliquely from above.

The holder 22 shown in FIG. 3 holds the pump tube 21 and fixed to the housing 11. The holder 22 is made of a hard synthetic resin material such as PC (polycarbonate), PETG (polyethylene terephthalate), acrylic resin, PVC resin, and Tritan (registered trademark), and is formed in a substantially rectangular shape in front view. The holder 22 is formed in a plate shape to have flexibility, and for example, is formed to have a flexural modulus of 500 MPa or more and 3500 MPa or less, preferably 1000 MPa or more and 3000 MPa or less. More specifically, the holder 22 includes a holder body 31, a pair of connector portions 32 and 33, and a pushing portion 34. The holder body 31 is a plate-shaped member having a substantially rectangular shape and flexibility when viewed from the front, and has a protrusion 35 at a central portion in the longitudinal direction (that is, the first direction). The protrusion 35 protrudes in the thickness direction of the holder body 31 from the back face 31*b* which is a surface opposite to the front face 31*a* of the holder body 31. Further, engagement portions 36 and 37 are formed at both ends of the holder body 31 in the longitudinal direction.

The two engagement portions 36 and 37 have shapes different from each other, and has a first engagement portion 36 at one end of the holder body 31 in the longitudinal direction (in the present embodiment, upper end) and has a second engagement portion 37 at the other end in the longitudinal direction (in the present embodiment, lower end). The first engagement portion 36 is formed at one end of the holder body 31 in the longitudinal direction so as to protrude from the front face 31*a* in the thickness direction, and has a substantially L-shape when viewed from the side. Note that the first engagement portion 36 does not necessarily need to protrude from the front face 31*a*, and may protrude from the back face 31*b*. Also, a guide 38 in addition to the first engagement portion 36 is formed at one end of the holder body 31 in the longitudinal direction. The guide 38 has a substantially elliptical shape when viewed from the side, and protrudes upward from one end in the longitudinal direction.

On the other hand, the second engagement portion 37 has four claw-shaped portions 37*a* to 37*d*, and the four claw-shaped portions 37*a* to 37*d* are disposed side by side at intervals in the short-side direction (the left-right direction in the present embodiment) at the other end of the holder body 31 in the longitudinal direction. More specifically, each of the claw-shaped portions 37*a* to 37*d* extends downward, and has a distal end formed in a substantially semi-cylindrical shape in side view. In addition, the distal end of each of the claw-shaped portions 37*a* to 37*d* protrudes in any of one thickness direction and the other thickness direction, and the claw-shaped portions 37*a* to 37*d* are disposed at the other end of the holder body 31 in the longitudinal direction such that the distal ends are positioned in a staggered manner (that is, the distal ends alternately protrude in one thickness direction and the other thickness direction).

The distal end side of the second engagement portion 37 configured as described above is formed so as to be substantially circular when viewed from the side, and is configured to be elastically deformable. That is, since the substantially semi-cylindrical portions of the claw-shaped portions 37*a* to 37*d* are disposed in a staggered manner, when the distal end portion of the second engagement portion 37 is pushed upward, each of the claw-shaped portions 37*a* to 37*d* moves so as to approach each other in side view, and the distal end portion of the second engagement portion 37 moves in the thickness direction and closes. As a result, the second engagement portion 37 is pushed upward, the holder body 31 contracts in the longitudinal direction, and the first engagement portion 36 can be pushed down. As described above, the engagement portions 36 and 37 are formed at both ends of the holder body 31 in the longitudinal direction, respectively. Further, a pair of connector portions 32 and 33 is integrally provided at an intermediate portion of the holder body 31 in the longitudinal direction.

Each of the pair of connector portions 32 and 33 is formed in a substantially cylindrical shape so that a liquid can flow therein, and is bent at an obtuse angle at an intermediate portion thereof. The pair of connector portions 32 and 33 having such a shape has insertion ports 32a and 33a at one end thereof. The angle formed by the opening direction of the insertion port 32a and the opening direction of the insertion port 33a is, for example, 47°. The insertion ports 32a and 33a are formed to have a large diameter with respect to the remaining portions of the connector portions 32 and 33, and the respective ends of the pump tube 21 are inserted and welded to the insertion ports 32a and 33a. Further, the pair of connector portions 32 and 33 has a supply port 32b and a discharge port 33b at the other end portion, the supply tube 2 is inserted and welded into the supply port 32b, and the discharge tube 3 is inserted and welded into the discharge port 33b. As a result, the supply tube 2 and the pump tube 21 communicate with each other via a supply side connector portion 32, and the pump tube 21 and the discharge tube 3 communicate with each other via a discharge side connector portion 33 (see FIG. 4). That is, the supply tube 2 and the discharge tube 3 communicate with each other via the pair of connector portions 32 and 33 and the pump tube 21. As a result, the liquid in the supply tube 2 can be supplied from the supply side connector portion 32 to the pump tube 21, and the liquid in the pump tube 21 can be discharged from the discharge side connector portion 33 to the discharge tube 3.

Figure 4:
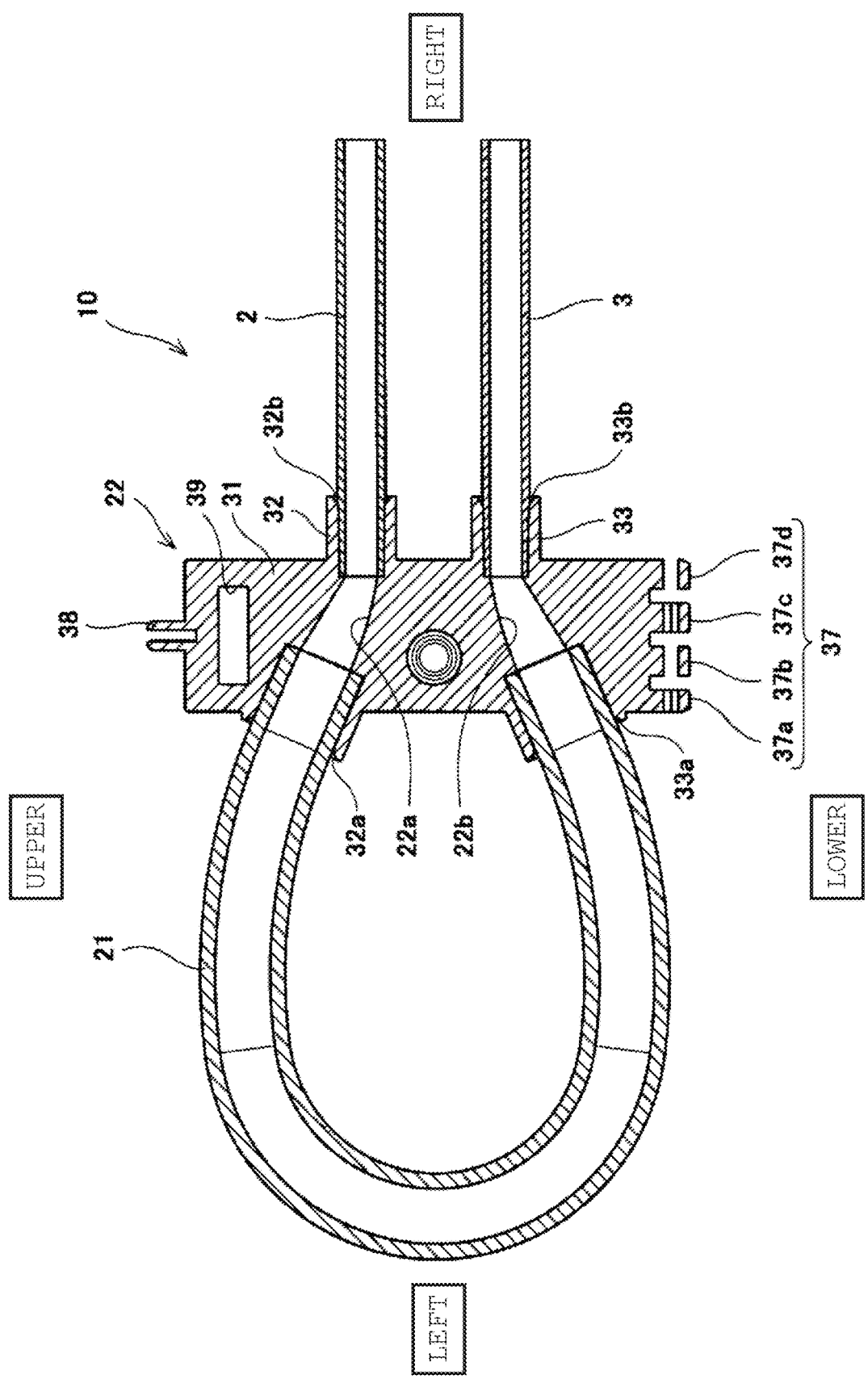
FIG. 4 is a cross-sectional view of the tube set of FIG. 1 cut away and viewed from the front.

In the present embodiment, the supply port 32b and the discharge port 33b are orthogonal to the holder body 31 and extend in parallel with each other. Further, as shown in FIG. 4, the inside of the supply port 32b and the inside of the discharge port 33b are formed in a cylindrical shape extending linearly. With such a configuration, the supply tube 2 and the discharge tube 3 can be attached to the holder body 31 without bending. As a result, the configuration is such that the burden due to the stress on the tube end is reduced.

The pair of connector portions 32 and 33 configured as described above extends in the shorter direction of the holder body 31 and is spaced apart in the longitudinal direction so as to sandwich the protrusion 35. The pair of connector portions 32 and 33 disposed in this manner is provided integrally in the holder body 31 as if the holder body 31 penetrates them. More specifically, in the pair of connector portions 32 and 33, the supply side connector portion 32 is disposed on the first engagement portion 36 side, and the discharge side connector portion 33 is disposed on the second engagement portion 37 side, so that the pair of connector portions 32 and 33 is away from each other in the longitudinal direction. In addition, the pair of connector portions 32 and 33 is disposed on a virtual plane in which the respective center axes are predetermined (a virtual plane showing a cross section shown in FIG. 4 when the tube set 10 is cut thereby), further, the holder body 31 is disposed along the virtual plane, and the holder body 31 and the pair of connector portions 32 and 33 disposed as described above are integrally formed. Further, the pair of connector portions 32 and 33 is oriented in a direction in which the insertion ports 32a and 33a are away from each other, that is, in an upper oblique direction and a lower oblique direction. As a result, the pump tube 21 is attached to the insertion ports 32a and 33a at its ends in a state where the pump tube 21 is curved in a substantially C shape. On the other hand, the supply port 32b and the discharge port 33b of the pair of connector portions 32 and 33 are orthogonal to the holder body 31, and extend parallel to each other, that is, to the right. The supply tube 2 and the discharge tube 3 of the blood circuit are attached to the supply port 32b and the discharge port 33b.

Further, the protrusion 35 of the holder body 31 protrudes in the thickness direction of the holder body 31, and the edge of the protrusion 35 is configured by a curved face that spreads as it approaches the face of the holder body 31. With such a configuration, the flexibility is reduced, and the strength of the holder body 31 is increased.

Further, a portion outside the visible outline of the holder body 31 of the insertion port 32a of the connector portion 32 of the present embodiment in plan view of FIG. 2, and a portion outside the visible outline of the holder body 31 of the insertion port 33a of the connector portion 33 in the plan view of FIG. 2 are not connected by the holder body 31. With such a configuration, the flexibility of the holder body 31 increases, and ease of attachment of the holder body 31 can be ensured without the strength becoming higher than necessary due to the provision of the protrusion 35.

Figure 5:
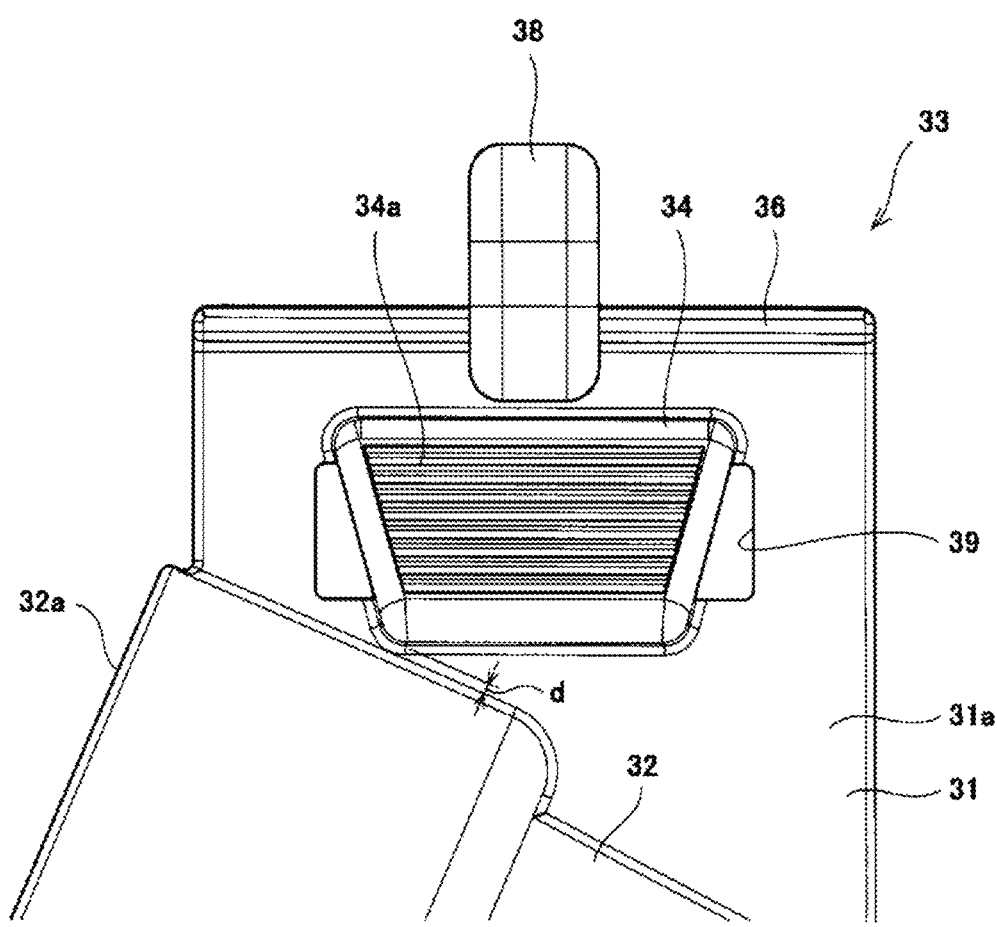
FIG. 5 is an enlarged front view of a pushing portion of the holder of FIG. 1 in an enlarged manner.

As shown in FIG. 5, a window 39 is formed in the holder body 31 between the supply side connector portion 32 and the first engagement portion 36. The window 39, which is an example of the weak portion, is formed in the holder body 31 so as to be away from the supply side connector portion 32 and the first engagement portion 36 in the longitudinal direction. The window 39 extends in the short direction and penetrates in the thickness direction. The window 39 thus formed facilitates bending of a portion between the supply side connector portion 32 and the first engagement portion 36 side. Further, the pushing portion 34 is integrally provided on the front face 31a of the holder body 31 so as to cover the window 39.

The pushing portion 34 is disposed so as to cross the window 39 in the longitudinal direction, and is formed in a substantially U shape when viewed from the right side (see also FIG. 6 described later). That is, the pushing portion 34 is formed to protrude in one thickness direction from the front face 31a of the holder body 31. Further, the pushing portion 34 has a placement face 34a at a position away from the front face 31a of the holder body 31 in one thickness direction. It is possible to press the placement face 34a with the finger cushion, and the placement face 34a is inclined so as to be away from the front face 31a, from the first engagement portion 36 toward the supply side connector portion 32, to be pressed with the finger cushion.

The pushing portion 34 configured as described above is disposed to be adjacent to the supply side connector portion 32, and the height of the pushing portion 34 and the inclination of the placement face 34a (that is, the angle with respect to the front face 31a) are set as follows. That is, the height of the pushing portion 34 and the inclination of the placement face 34a are set such that the virtual plane P1 including the placement face 34a is in contact with the outer peripheral face of the supply side connector portion 32. As a result, the finger placed on the placement face 34a can also be placed on the outer peripheral face of the supply side connector portion 32, so that the supply side connector portion 32 as well as the pushing portion 34 can be pushed together. On the other hand, although the pushing portion 34 is adjacent to the discharge side connector portion 33, it is disposed away from the supply side connector portion 32 so as not to be integrated with the supply side connector portion 32 (that is, does not contact) (see the distance d in FIG. 5). By doing so, the flexibility of the holder body 31 is prevented from lowering, and the holder body 31 is easily bent. Further, in the holder body 31, the pushing portion 34 is formed in a substantially U-shaped hollow shape, so that the flexibility of the holder body 31 is prevented from lowering and the holder body 31 is easily bent.

The tube set 10 configured in this way pumps out the liquid therein by squeezing the pump tube 21, and is detachably fixed to the housing 11 for squeezing the pump tube 21 as shown in FIG. 1. That is, the housing 11 has an accommodation recess 41 for accommodating the tube set 10. The accommodation recess 41 is a recess extending in the left-right direction, and is a substantially U-shaped recess when viewed from the front. That is, the left side of the accommodation recess 41 is formed in a substantially semicircular shape, and the opening 11a is formed on the right side of the accommodation recess 41. The accommodation recess 41 has a holder accommodation region 41a in a region near the opening 11a, and has a tube accommodation region 41b in the remaining region. The holder 22 of the tube set 10 is disposed in the holder accommodation region 41a, where the holder 22 is fixed to the housing 11. Further, the pump tube 21 is accommodated in the tube accommodation region 41b. More specifically, the pump tube 21 is accommodated along the inner peripheral face 11b of the housing 11 that defines the tube accommodation region 41b. Further, in the tube accommodation region 41b, the rotor 12 is disposed so as to be located inside the pump tube 21. That is, the pump tube 21 is disposed between the inner peripheral face 11b of the housing 11 and the rotor 12, and is squeezed by the rotor 12.

The rotor 12 includes a rotor body 42, a pair of rollers 43 and 43, and a pair of guide pins 44 and 44. The rotor body 42 is formed in a substantially hexagonal shape that is horizontally long in the left-right direction, and is provided on the housing 11 so as to be rotatable about its center of gravity. More specifically, the rotor body 42 is disposed in the tube accommodation region 41b in a state away from the inner peripheral face 11b of the housing 11, and is provided on the housing 11 such that the center of gravity overlaps the center axis L1 of the substantially semicircular portion of the tube accommodation region 41b. Further, the pair of rollers 43 and 43 is rotatably attached to the rotor body 42 so as to squeeze the pump tube 21. More specifically, the pair of rollers 43 and 43 is disposed at opposite sides, of the rotor body 42, that are away from each other in the longitudinal direction thereof, and is shifted from each other by 180 degrees. Note that, in the present embodiment, the pair of rollers 43 and 43 is disposed so as to be located at a pair of diagonal positions shifted from each other by 180 degrees in the rotor body 42. The roller 43 disposed in this manner is formed in a substantially cylindrical shape, and a rotation shaft (not shown) is inserted therein. The rotation shaft is supported by the rotor body 42 so as to be parallel to the center axis L1, and the roller 43 can rotate around the rotation axis.

The pair of rollers 43 and 43 configured as described above is pressed against or away from the pump tube 21 according to the angular position around the center axis L1. That is, the roller 43 is away from the pump tube 21 when it is located at about 0 degrees as in the right roller 43 in FIG. 1, and the roller 43 contacts the pump tube 21 and presses the pump tube 21 against the inner peripheral face 11b of the housing 11 when rotated counterclockwise to about 45 degrees. From there, the roller 43 further rotates counterclockwise, so that the roller 43 squeezes the pump tube 21 to press the pump tube 21 against the inner peripheral face 11b (see the left roller 43 in FIG. 1). Thereby, the liquid in the pump tube 21 is fed out counterclockwise. Afterwards, the roller 43 is away from the pump tube 21 when the rotor 12 is rotated counterclockwise to about 315 degrees, and continues to be away from the pump tube 21 until the roller 43 reaches a position of about 45 degrees at which the roller 43 contacts the pump tube 21 again.

As described above, the rotor 12 can perform the feeding operation by rotating the rollers 43 and 43 around the center axis L1. Also, since the pair of rollers 43 and 43 is disposed with each shifted by 180 degrees, at least one of the pair of rollers 43 and 43 is squeezing the pump tube 21 while the rotor 12 is rotating, so that the liquid in the pump tube 21 is prevented from returning. Therefore, the liquid in the pump tube 21 can be fed out by rotating the rotor body 42. An electric motor (not shown) is attached to the rotor body 42. More specifically, the electric motor is disposed on the back side of the housing 11 (that is, on the back side of the drawing of FIG. 1), and has an output shaft that can be driven to rotate. The output shaft penetrates the housing 11 along the center axis L1, and is attached to the rotor body 42. The rotor body 42 is attached to the housing 11 so as to be rotatable about the center axis L1 as described above, and is configured to rotate about the center axis L1 when the output shaft rotates.

Thus, in the tube pump 1, the pump tube 21 can be disposed between the rotor 12 and the inner peripheral face 11b of the housing 11, and the liquid can be fed out by squeezing the pump tube 21 by the roller 43 of the rotor 12. Further, the rotor 12 is formed to be horizontally long so as to squeeze the pump tube 21, and as shown in FIG. 1, the portion between the laterally protruding portions 12R and 12L of the rotor 12 and the inner peripheral face 11b is reduced. Therefore, the rotor body 42 is provided with the guide pin 44 for fitting the pump tube 21 between the rotor 12 and the inner peripheral face 11b since the pump tube 21 cannot be easily fitted. The guide pin 44 is provided in the rotor body 42 in the counterclockwise front direction of each roller 43, and protrudes from the rotor body 42 in a direction perpendicular to the center axis L1.

The guide pins 44 disposed in this way function as follows when the pump tube 21 is attached. That is, the rotor body 42 is rotated counterclockwise in a state where the guide pins 44 are disposed on the front side of the pump tube 21 (on the front side of the drawing of FIG. 1). The guide pins 44 rotate while pressing the pump tube 21 against the back side face of the housing 11, and one rotation of the rotor body 42 causes the entire pump tube 21 to be accommodated between the inner peripheral face 11b of the housing 11 and the rotor 12. On the other hand, the rotor body 42 is rotated counterclockwise in a state in which the guide pin 44 is disposed on the back side of the pump tube 21 (on the back side of the drawing of FIG. 1), that is, in a state where the guide pin 44 is inserted between the pump tube 21 and the housing 11. The pump tube 21 is peeled off from the housing 11, and the pump tube 21 can be removed from the tube accommodation region 41b. Although in the present embodiment, the pump tube 21 is mounted and removed by rotating the rotor body 42 counterclockwise, the pump tube 21 may be mounted and removed by rotating the rotor body 42 clockwise.

Thus, the tube pump 1 is configured such that the pump tube 21 is detachable. Therefore, the holder 22 is attached to the housing 11 and the tube set 10 is attached to the housing 11 so that the pump tube 21 attached does not come off the housing 11 when the liquid is being fed out. In order to attach the holder 22 to the housing 11, the housing 11 has a holder accommodation region 41a near the opening 11a as described above, and the holder 22 fits into the holder accommodation region 41a.

Figure 6:
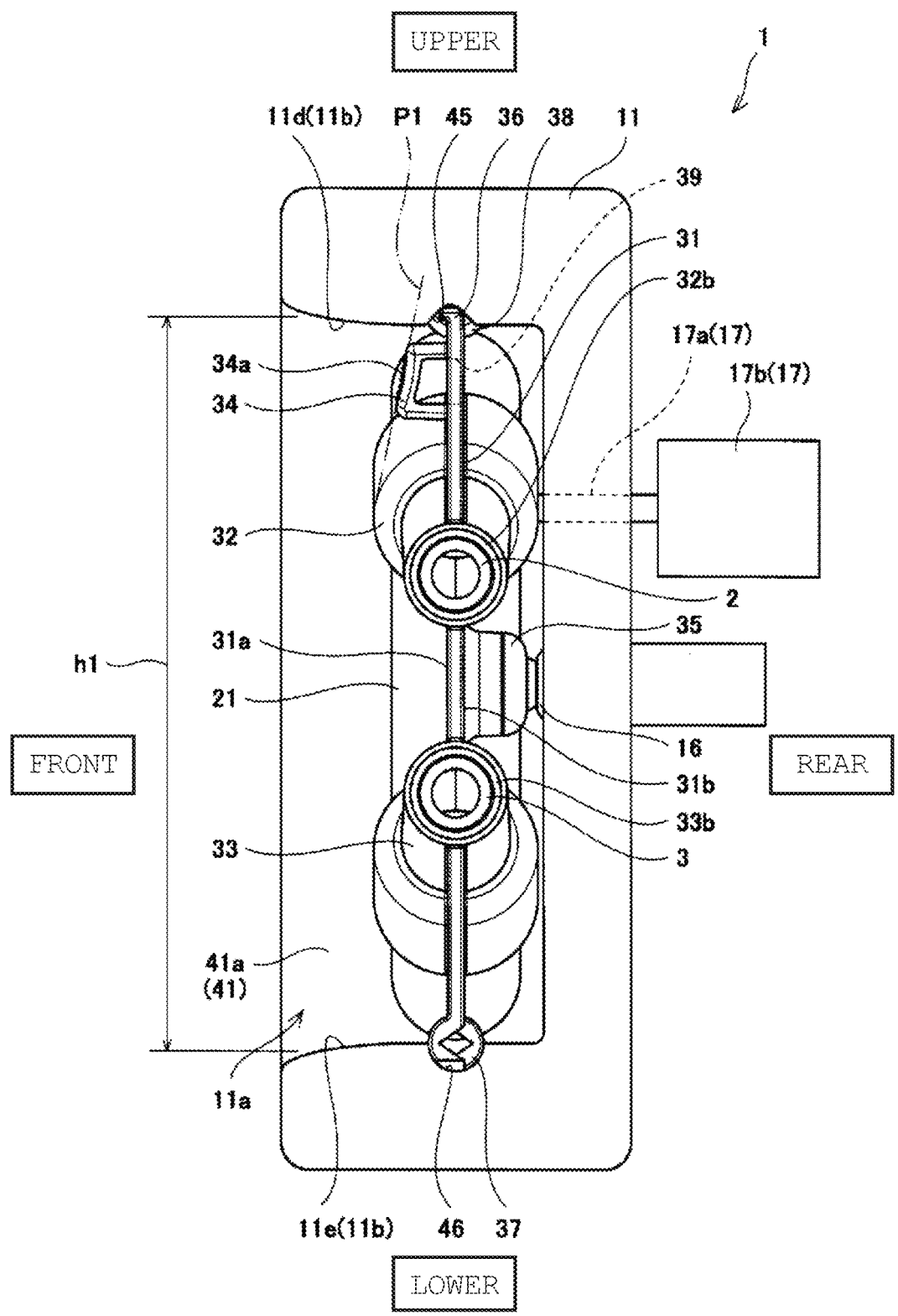
FIG. 6 is a right side view of the tube pump of FIG. 1 as viewed from the right side.

More specifically, as shown in FIG. 6, the inner peripheral face 11b of the housing 11 has vertically opposing portions 11d and 11e to define the holder accommodation region 41a, and the opposing portions have a pair of engagement grooves 45 and 46 extending in the left-right direction, respectively. In FIG. 6, the illustration of the rotor 12 and the cover 13 is omitted. The pair of engagement grooves 45 and 46 is formed so as to be vertically recessed in the opposing portions 11d and 11 e of the inner peripheral face 11b so as to face each other in the vertical direction. The first engagement groove 45, which is the upper engagement groove, is formed so that the first engagement portion 36 of the holder 22 can be fitted therein, and the second engagement groove 46, which is the lower engagement groove, is formed so that the second engagement portion 37 of the holder 22 can be fitted therein. Also, the housing 11 has a guide groove 47 extending in the front-rear direction (i.e., the front side and the back side in FIG. 1) at a position corresponding to the guide 38 of the holder body 31 (see FIG. 1), and the guide 38 is guided by the guide groove 47 by inserting the guide 38 into the guide groove 47.

In the housing 11 configured as described above, the holder 22 is mounted and fixed to the housing 11 by the following operation. That is, first, the second engagement portion 37 of the holder 22 is fitted into the second engagement groove 46 of the housing 11, and then the first engagement portion 36 is fitted into the first engagement groove 45. Thereby, the holder 22 can be fixed to the housing 11 in a state of being accommodated in the holder accommodation region 41a. In the housing 11, the opposing portions 11d and 11 e of the inner peripheral face 11b of the housing 11 have the following shape in order to prevent the fixed holder 22 from easily coming out of the holder accommodation region 41a. That is, the pair of opposing portions 11d and 11e is formed in a tapered shape on the front side of the respective engagement grooves 45 and 46, and the holder accommodation region 41a expands toward the front side from each of the engagement grooves 45 and 46. That is, the height h1 of the holder accommodation region 41a (that is, the interval between the surfaces facing each other) is gradually reduced from the front side toward the back side. Also, the height h1 of the holder accommodation region 41a is higher than the height h2 of the holder body 31 of the holder 22 on the most front side, and it is slightly shorter than h2 on the most back side (that is, the length in the longitudinal direction). Therefore, the holder 22 cannot be disengaged from the engagement grooves 45 and 46 without bending, and cannot be easily removed from the housing 11. The depth of each of the engagement grooves 45 and 46 is set according to the height of the holder 22. Accordingly, the fixed holder 22 is sandwiched between the pair of opposing portions 11d and 11 e without bending, and the movement in the vertical direction is restricted so as not to rattle. The housing 11 configured as described above has a detection switch 16 and a reject mechanism 17.

The detection switch 16 is disposed at a position corresponding to the protrusion 35 of the holder body 31, and comes into contact with the protrusion 35 when the holder 22 is accommodated in the holder accommodation region 41a and fixed to the housing 11. The detection switch 16 detects that the holder 22 has been fixed by the contact of the protrusion 35, and outputs the detection to the control unit of the dialysis device (not shown). The reject mechanism 17 is a mechanism for removing the holder 22 from the housing 11, and has a reject pin 17a and a direct drive motor 17b. The reject pin 17a penetrates the housing 11 on the front side and protrudes into the holder accommodation region 41a, and is configured to be able to move in front-rear direction in the protruding state. In addition, the reject pin 17a is disposed at a position corresponding to the supply port 32b, and comes into contact with the supply port 32b by moving forward. By further advancing in the contact state, this portion is pushed forward, the first engagement portion 36 is disengaged from the first engagement groove 45, and the holder 22 is detached from the housing 11. The reject pin 17a that operates as described above is provided on the direct drive motor 17b so as to automatically perform the operation, and is driven by the direct drive motor 17b so as to be able to move in the front-rear direction. Accordingly, the holder 22 can be automatically removed from the housing 11 by giving a signal from the control unit of the dialysis device to the direct drive motor 17b.

The housing 11 is provided with the cover 13 made of a transparent synthetic resin. The cover 13 is configured to cover the entire accommodation recess 41 from the front, and is rotatably attached to a hinge 11c of the housing 11. The cover 13 configured as described above can cover the accommodation recess 41 by its rotation.

<Method of Attaching and Detaching Tube Set>

In the tube pump 1 configured as described above, the tube set 10 is attached to the housing 11 as described below. That is, in the tube set 10, the supply tube 2 is inserted into the supply side connector portion 32 of the holder 22 in advance, and the discharge tube 3 is inserted into the discharge side connector portion 33. That is, the tube set 10, together with the supply tube 2 and the discharge tube 3, constitutes a blood circuit in advance. In this state, the tube set 10 is mounted on the housing 11, and at the time of mounting, the holder 22 is first mounted on the housing 11. More specifically, first, the second engagement portion 37 of the holder 22 is fitted into the second engagement groove 46 of the housing 11. After the fitting, the holder 22 is raised to the back side of the housing 11 with the second engagement portion 37 as a fulcrum by pressing the holder 22 with a finger or the like. At this time, the left and right positions of the holder 22 are adjusted so that the guide 38 of the holder 22 enters the guide groove 47. Then, the guide 38 enters the guide groove 47 while being raised, and the first engagement portion 36 contacts the inner peripheral face 11b of the housing 11 (more specifically, the opposing portion 11d). From such a state, a finger is placed on the placement face 34a of the pushing portion 34 and the supply side connector portion 32 in order to further push the holder 22 to the back (that is, the holder accommodation region 41a).

After the finger is placed and the pushing portion 34 and the supply side connector portion 32 are pushed into the holder accommodation region 41a with the finger, the first engagement portion 36 is pressed against the opposing portion 11d, and accordingly, a portion between the first engagement portion 36 and the supply side connector portion 32 is bent so as to fall to the front. By the bending, the position of the first engagement portion 36 is lowered, and by the lowering, the first engagement portion 36 can be advanced to the back along the inner peripheral face 11b. Further, when the portion between the first engagement portion 36 and the supply side connector portion 32 falls, the second engagement portion 37 is also pushed downward. Thereby, the four claw-shaped portions 37a to 37d of the second engagement portion 37 move so as to approach each other in side view, and the second engagement portion 37 contracts. This also contributes to lowering the position of the first engagement portion 36 and moving the first engagement portion 36 to the back along the opposing portion 11d. As described above, the first engagement portion 36 is easily moved to the back side by bending the portion between the first engagement portion 36 and the supply side connector portion 32 and contracting the second engagement portion 37. By advancing the first engagement portion 36 to the back side in this way, a portion of the holder 22 other than a portion between the first engagement portion 36 and the supply side connector portion 32 rise. When the holder 22 is further pushed into the holder accommodation region 41a with a finger, the first engagement portion 36 reaches the first engagement groove 45 and is fitted therein. Thereby, both ends of the holder 22 in the longitudinal direction are engaged with the pair of engagement grooves 45 and 46, that is, the holder 22 is mounted and fixed to the housing 11.

In the tube set 10, the material and the shape of each part of the holder 22 are set so that the holder 22 becomes hard, for example, the flexural modulus of the holder 22 is 500 MPa or more and 3500 MPa or less (preferably, 1000 MPa or more and 3000 MPa or less). Thereby, a click feeling when the holder 22 is mounted on the housing 11 can be obtained. For example, the click feeling is obtained by the impact sound (i.e., click sound) generated when the vicinity of the first engagement portion 36 of the holder 22 elastically returns when the first engagement portion 36 is fitted into the first engagement groove 45, and thereby, the impact transmitted to the finger through the impact sound. By generating such a click feeling, it is possible to check whether the holder 22 is accurately fixed to the housing 11 by sound or response. It should be noted that a relatively soft material such as PP does not have the flexural modulus as described above, and it is difficult to obtain an impact sound or an impact response. Therefore, it is possible to prevent the tube pump 1 from performing an undesired operation due to incomplete mounting.

In such a fixed state, the laterally protruding portions 12R and 12L of the rotor 12 are disposed so as to be located on the left and right, respectively. In this state, the pump tube 21 is placed on the right protruding portion 12R of the rotor 12. On the other hand, the left protruding portion 12L is located near both ends of the pump tube 21 which is largely away. In such a state, the following storage operation is performed in order to accommodate the pump tube 21 mounted on the right protruding portion 12R between the inner peripheral face 11b of the housing 11 and the rotor 12. That is, by fixing the holder 22 to the housing 11, the vicinity of both ends of the pump tube 21 is disposed so as to approach the back side face of the housing 11. Therefore, the vicinity of both ends of the pump tube 21 is located on the back side relative to the guide pin 44 of the rotor 12, and when the rotor 12 is rotated counterclockwise, the guide pin 44 rotates while pressing the pump tube 21 against the back side face of the housing 11. The pump tube 21 is sandwiched between the roller 43 located on the back side of the guide pin 44 in the rotation direction and the inner peripheral face 11b of the housing 11, and by one rotation of the guide pin 44 around the center axis L1, the entire pump tube 21 is accommodated between the inner peripheral face 11b of the housing 11 and the rotor 12. When the entire pump tube 21 is thus accommodated between the inner peripheral face 11b of the housing 11 and the rotor 12, the accommodation recess 41 is thereafter closed by the cover 13. Thus, the attachment of the tube set 10 to the housing 11 is completed. After the attachment is completed, when the inside of the pump tube 21 is filled with a liquid such as blood or a drug solution, and the rotor 12 is driven counterclockwise in this state to squeeze the pump tube 21, the liquid will be fed from the supply tube 2 through the pump tube 21 to the discharge tube 3.

Next, a method of removing the pump tube 21 from the housing 11 will be described. First, a signal is given from the control device to the reject mechanism 17. Then, the direct drive motor 17b of the reject mechanism 17 is driven to move the reject pin 17a forward. The reject pin 17a eventually contacts the holder 22 (more specifically, the supply port 32b), and pushes the holder 22 to the front when the reject pin 17a further moves forward. When pressed, the portion between the first engagement portion 36 and the supply side connector portion 32 of the holder 22 bends so as to protrude to the front. Further, when pressed, the claw-shaped portions 37a to 37d of the second engagement portion 37 move so as to approach each other in side view, and the second engagement portion 37 contracts. As a result, the position of the first engagement portion 36 is lowered, and the first engagement portion 36 is away from the first engagement groove 45. After the detachment, the control device further advances the reject pin 17a. Then, the holder 22 falls to the front with the second engagement portion 37 as a starting point while sliding the first engagement portion 36 against the inner peripheral face 11b, and the first engagement portion 36 is away from the opposing portion 11d of the inner peripheral face 11b when pushed further. Then, the second engagement portion 37 can be removed from the second engagement groove 46, and the holder 22 can be removed from the housing 11.

On the other hand, the pump tube 21 remains accommodated between the inner peripheral face 11b of the housing 11 and the rotor 12, and the following removal operation is performed by the rotor 12 in order to remove the pump tube 21 from therebetween. That is, when the pump tube 21 is removed, similarly to the case where the pump tube 21 is fixed, the laterally protruding portions 12R and 12L of the rotor 12 are disposed so as to be located on the left and right, respectively. On the other hand, the vicinity of both ends of the pump tube 21, in particular, one end attached to the supply side connector portion 32, is away from the back side face of the housing 11 by removing the holder 22. Therefore, one end of the pump tube 21 is located on the front side relative to the guide pin 44 of the rotor 12, and when the rotor 12 is rotated counterclockwise, the guide pin 44 rotates while entering a space between the pump tube 21 and the back side face of the housing 11. Then, the pump tube 21 is away from the back side face of the housing 11 by the guide pin 44 and is pushed out toward the front side of the rotor 12, and by one rotation of the guide pin 44 around the center axis L1, the entire pump tube 21 is pushed out toward the front side of the rotor 12. In this way, the entire pump tube 21 is pushed out of the rotor 12 toward the front side, the tube set 10 can be removed from the housing 11, and in this state, the cover 13 is opened and the tube set 10 is removed from the housing 11.

In the tube set 10 configured as described above, since the holder body 31 and the connector portions 32 and 33 are integrated, the number of components of the tube set 10 can be reduced. Also, since the pump tube 21 is directly inserted and welded into the connector portions 32 and 33 formed integrally with the holder body 31, the work of attaching the connector portions 32 and 33 to the holder body 31 can be omitted. Therefore, man-hours for assembling the tube set 10 can be reduced.

Furthermore, in tube set 10, as described above, after the second engagement portion 37 is fitted into the second engagement groove 46, the holder 22 is inserted into the accommodation recess 41 by bending mainly the portion between the first engagement portion 36 and the supply side connector portion 32, and further pressed to fit the first engagement portion 36 into the first engagement groove 45. Therefore, a weak portion such as the window 39 is formed in the vicinity of the first engagement portion 36, so that the vicinity of the first engagement portion 36 of the holder 22 is easily bent. In the holder 22, by configuring the pushing portion 34 and the supply side connector portion 32 apart, the rigidity of the holder 22 is prevented from increasing, and the vicinity of the supply side connector portion 32 of the holder 22 is easily bent. In this way, in the holder 22, the portion between the first engagement portion 36 and the supply side connector portion 32 easily bends, so that even when the holder 22 is made of a hard material as described above, the holder 22 can be easily inserted into the accommodation recess 41, and the difficulty in mounting the holder 22 to the housing 11 due to the change of the material can be eliminated. In addition, even when a hard material is used, the holder 22 can have transparency by using the above-described material, and the flow of the liquid in the tube set 10 and the bubbles contained in the liquid can be seen.

Further, in the tube set 10, a finger placed on the placement face 34$a$ of the pushing portion 34 can also be put on the supply side connector portion 32. Accordingly, not only the placement face 34$a$ but also the supply side connector portion 32 can be pushed, and the area pressed by a finger can be made large, compared with the case in which only the placement face 34$a$ is pushed with a finger. Accordingly, the area of the placement face 34$a$ itself can be reduced, and the rigidity of the holder 22 can be prevented from increasing. In addition, since the area that can be pressed by a finger is increased, a load is easily applied to the holder 22, and a larger load can be applied to the holder 22.

Further, in the connector portions 32 and 33, the supply port 32$b$ and the discharge port 33$b$ are disposed away from each other. With this configuration, although not shown, the supply tube 2 and the discharge tube 3 can intersect with a margin. Therefore, the stress acting on these tubes can be reduced, and the deterioration of the tubes can be further suppressed. In the present embodiment, the supply tube 2 and the supply port 32$b$ are located on the upper side, and the discharge tube 3 and the discharge port 33$b$ are located on the lower side (that is, a configuration in which blood flows counterclockwise), but the configuration is provided for convenience of explanation, and the supply tube and the supply port, and the discharge tube and the discharge port may be upside down (that is, a configuration in which blood flows clockwise).

Second Embodiment

Next, a tube set according to a second embodiment of the present invention will be described with reference to the drawings. The embodiment described below differs from the tube set according to the first embodiment in the problem to be solved. In the tube set described in PTL 1, the hoses 16 and 18 are fixed in the connector 14, and the connection ends of the hoses 16 and 18 and the connector 14 are bent, so that there is a concern that the load on the tube is increased and the tube is likely to deteriorate. An object of the present embodiment is to reduce the load on the tube and obtain a tube set with high reliability during use. First, a description will be given of a holder 122 provided in the tube set shown in FIG. 10 described later. Note that, in the present embodiment, the same components as those in the first embodiment are denoted by the same reference numerals, and description thereof will be omitted.

Figure 7:
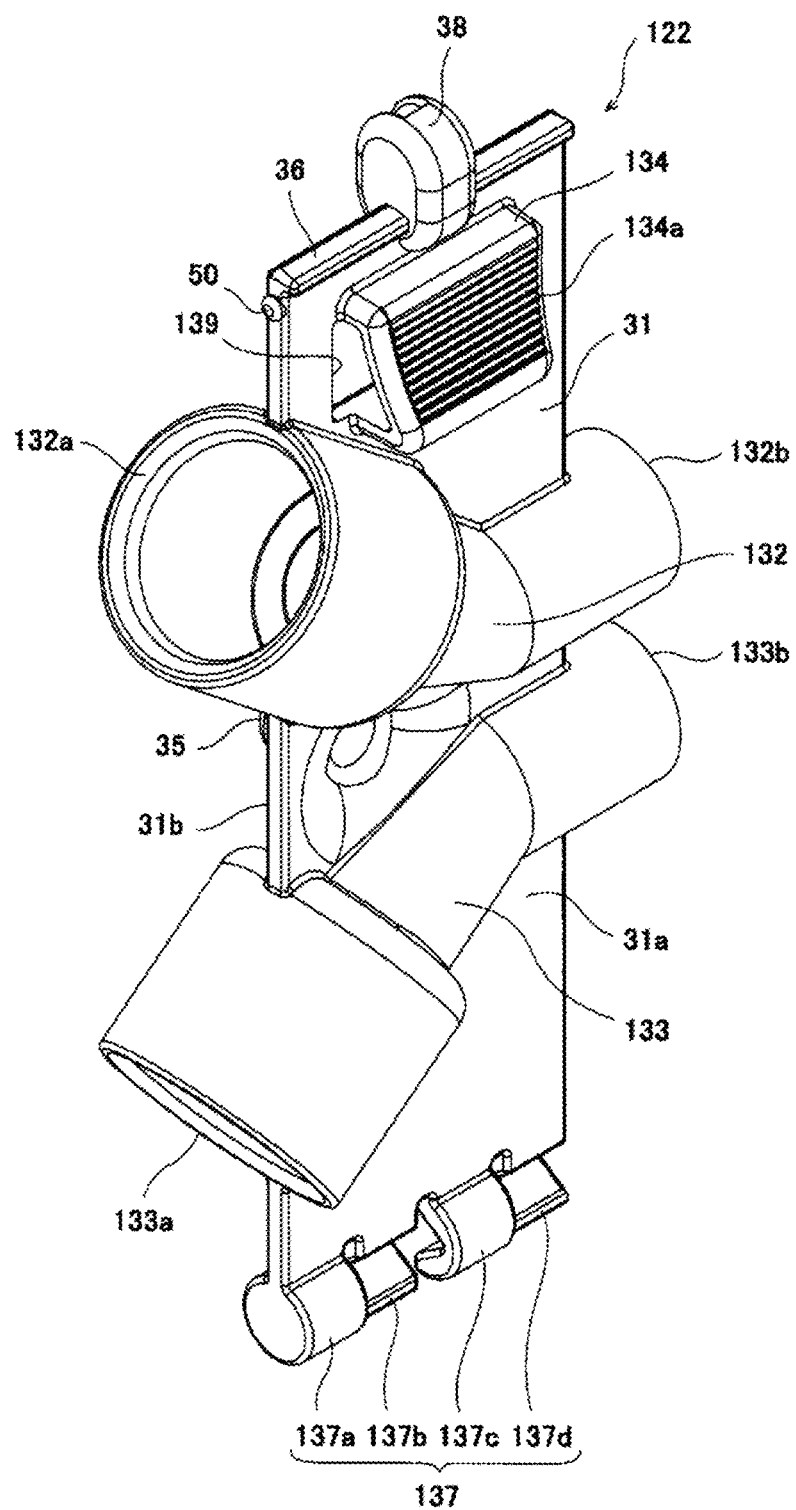
FIG. 7 is a perspective view of a holder according to a second embodiment of the present invention.
Figure 8A:
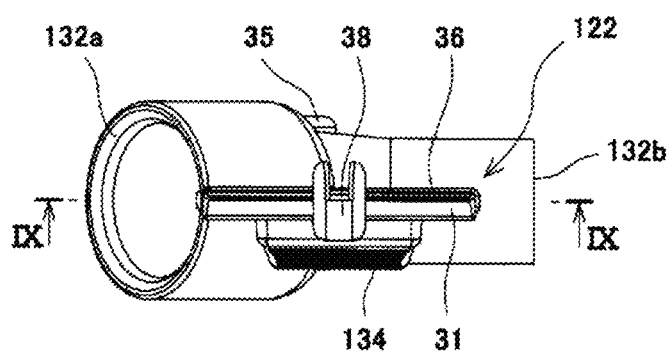
FIG. 8(*a*) is a plan view of the holder of FIG. 7, and FIG. 8(*b*) is a front view of the holder of FIG. 7.

In the second embodiment, as shown in FIGS. 7 and 8($b$), in the holder 122, the angle $\alpha$ (see FIG. 8($b$)) formed by the opening direction of an insertion port 132$a$, of a connector portion 132, into which one end of the pump tube 21 (see FIG. 10) is inserted, and an insertion port 133$a$, of a connector portion 133, into which the other end of the pump tube 21 is inserted is made larger than that in the first embodiment. Specifically, the angle $\alpha$ is 55° to 120°, preferably 60° to 90°. Note that, also in the present embodiment, in the connector portions 132 and 133, a supply port 133$b$ and a discharge port 132$b$ are configured to be away from each other, but this is defined for convenience of explanation. The supply port and the discharge port may be located upside down, and the supply tube connected to the supply port and the discharge tube connected to the discharge port may be located upside down accordingly.

Further, similarly to the first embodiment, also in the present embodiment, the inside of the supply port 132$b$ and the inside of the discharge port 133$b$ are formed in a cylindrical shape extending linearly. With such a configuration, the supply tube 2 and the discharge tube 3 can be attached to the holder body 31 without bending. As a result, the configuration is such that the burden due to the stress on the tube end is reduced.

Further, similarly to the first embodiment, the protrusion 35 of the holder body 31 protrudes in the thickness direction of the holder body 31, and the edge of the protrusion 35 is formed of a curved face that expands as it approaches the face of the holder body 31. With such a configuration, the flexibility is reduced, and the strength of the holder body 31 is increased.

Further, similarly to the first embodiment, a portion outside the visible outline of the holder body 31 of the insertion port 132$a$ of the connector portion 132 of the present embodiment in plan view of FIG. 8($b$) and a portion outside the visible outline of the holder body 31 of the insertion port 133$a$ of the connector portion 133 in plan view of FIG. 8($b$) are not connected by the holder body 31. With such a configuration, the flexibility of the holder body 31 increases, and ease of attachment of the holder body 31 can be ensured without the strength becoming higher than necessary due to the provision of the protrusion 35.

Here, the pump tube 21 is packed in a state of being inserted into the connector portions 132 and 133 of the holder 122, and may be stored for several years until it is used. Therefore, the shape of the pump tube 21 may change during this period. More specifically, as the stress continues to be applied to the curved portion of the pump tube 21 with time, the curvature of the portion increases (the radius of curvature decreases). That is, in the pump tube 21, the dimension from the holder 122 to the curved portion of the pump tube 21 gradually increases. For this reason, when using tube pump 1, when setting the pump tube 21 in the housing 11 and closing the cover 13, there is a possibility that the curved portion of the pump tube 21 comes into contact with the hinge 11$c$ and the cover 13 cannot be closed.

Figure 10:
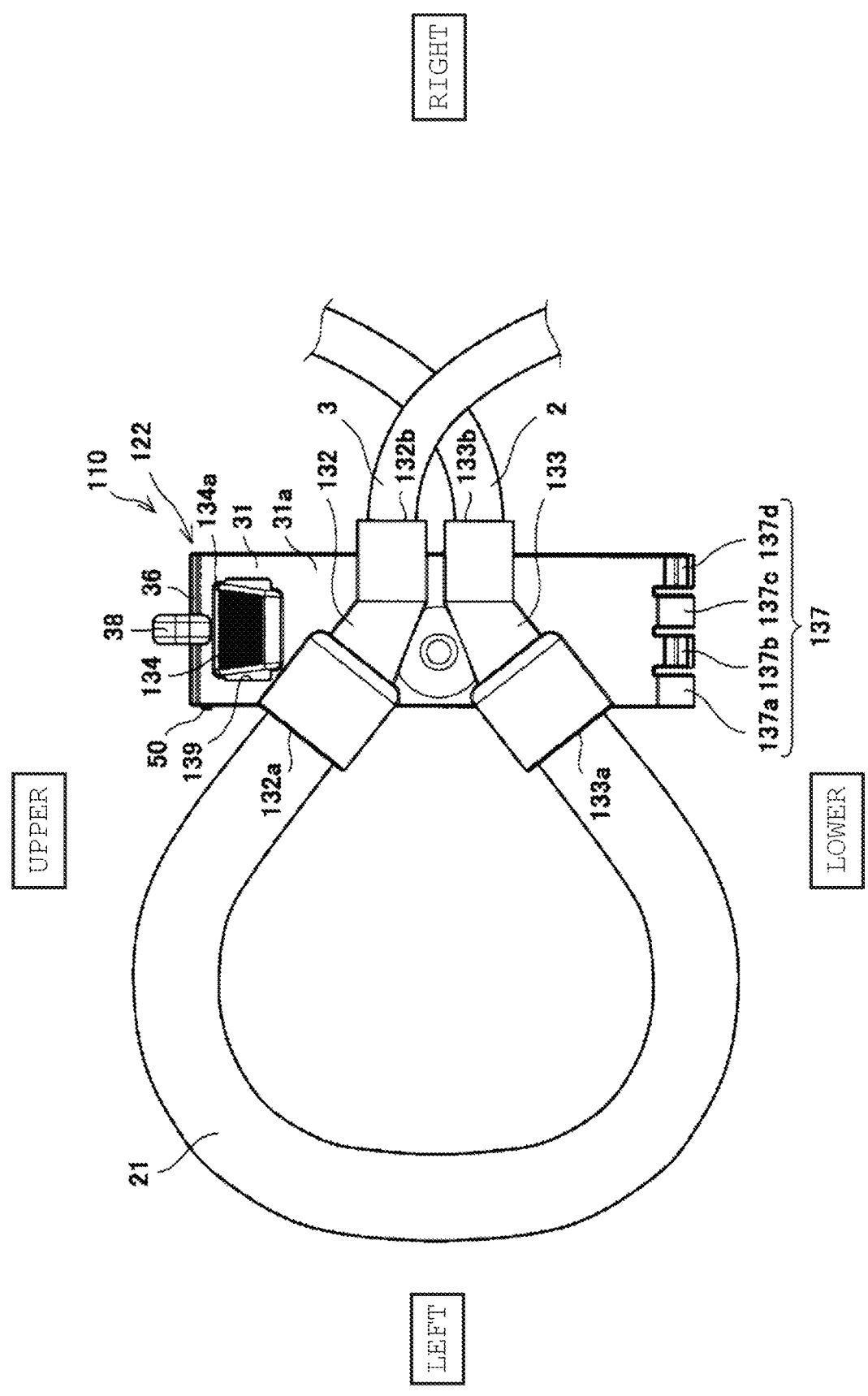
FIG. 10 is a front view of a tube set according to the second embodiment of the present invention.
Figure 11:
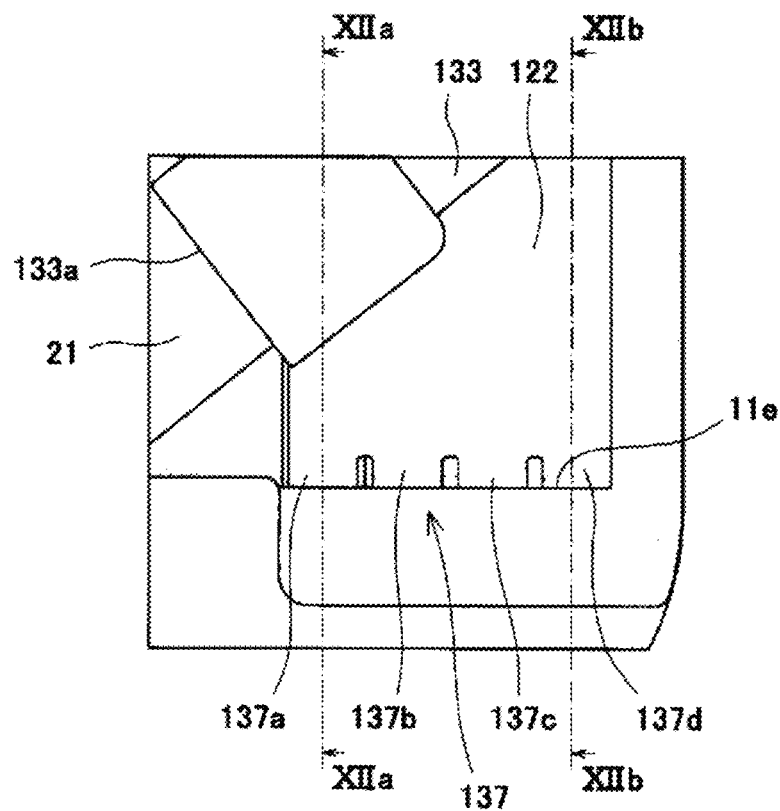
FIG. 11 is a front view showing part of a tube pump according to the second embodiment of the present invention.

Therefore, as mentioned above, by making the angle $\alpha$ larger than that in the first embodiment, the curvature of the curved portion of the pump tube 21 can be made smaller (the radius of curvature is larger) than that in the first embodiment as shown in FIG. 10. Further, with such a configuration, it is not necessary to perform the annealing step for preventing the above-described event that the curvature of the curved portion of the pump tube 21 increases with time. Thus, there is no adverse effect due to the additional annealing step, such as deterioration of the pump tube 21 due to heating and cost increase due to additional steps. Furthermore, even when the angle α is set to be limited to the above-described range, similarly to the first embodiment, the configuration in which the supply port 133b and the discharge port 132b are disposed away from each other is ensured. Thereby, the supply tube 2 and the discharge tube 3 can intersect with each other with a margin. Thereby, the stress on the supply tube 2 and the discharge tube 3 can be reduced.

Figure 9:
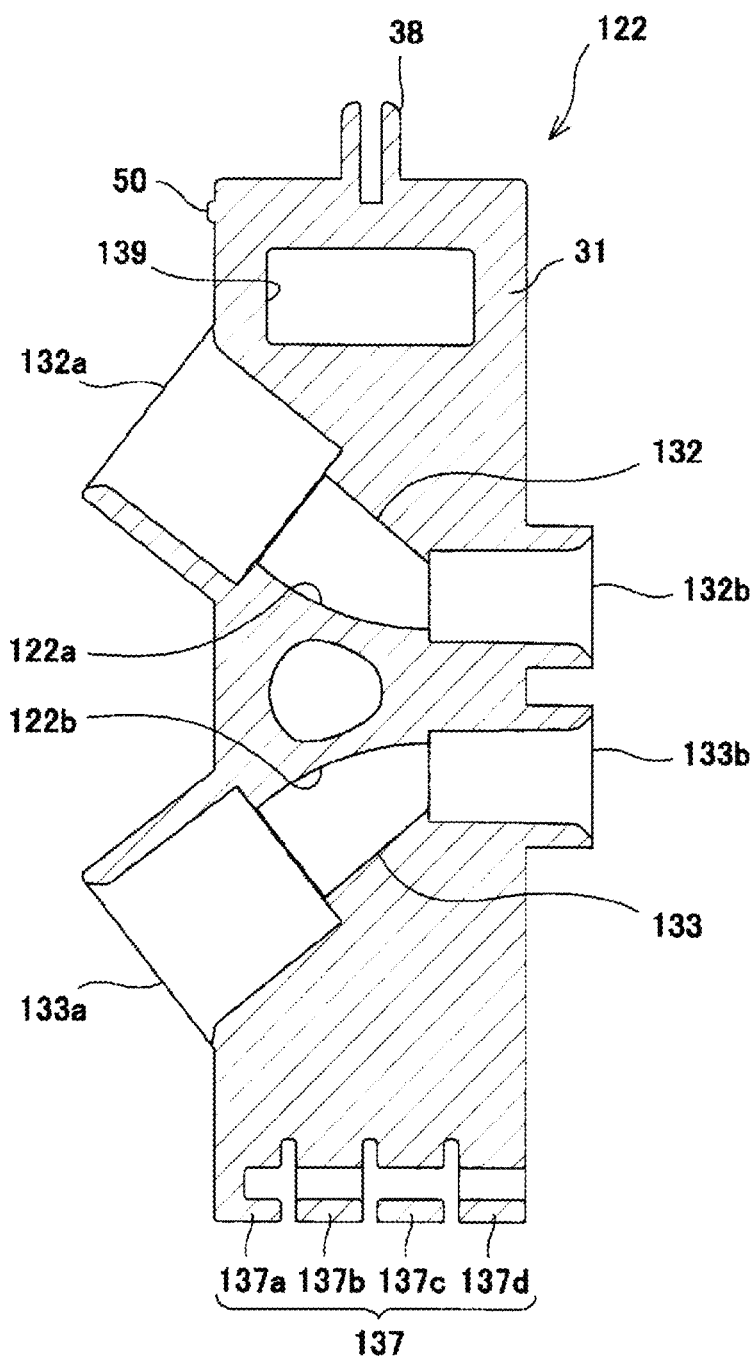
FIG. 9 is a sectional view taken along line IX-IX of FIG. 8(*a*).

As described above, by making the angle α larger than that in the first embodiment, the interval between the discharge port 132b of the connector portion 132 and the supply port 133b of the connector portion 133 is smaller than that of the first embodiment, and the curvature of each hole of the connector portions 132 and 133 is increased so that pins for forming the holes of the connector portions 132 and 133 shown in FIG. 9 are not forcibly removed when molding the holder 122. In the present embodiment, unlike the first embodiment, the supply port and the discharge port are located upside down, but this is defined for convenience of explanation. The supply port and the discharge port may be located upside down, and the supply tube connected to the supply port and the discharge tube connected to the discharge port may be located upside down accordingly.

Figure 8B:
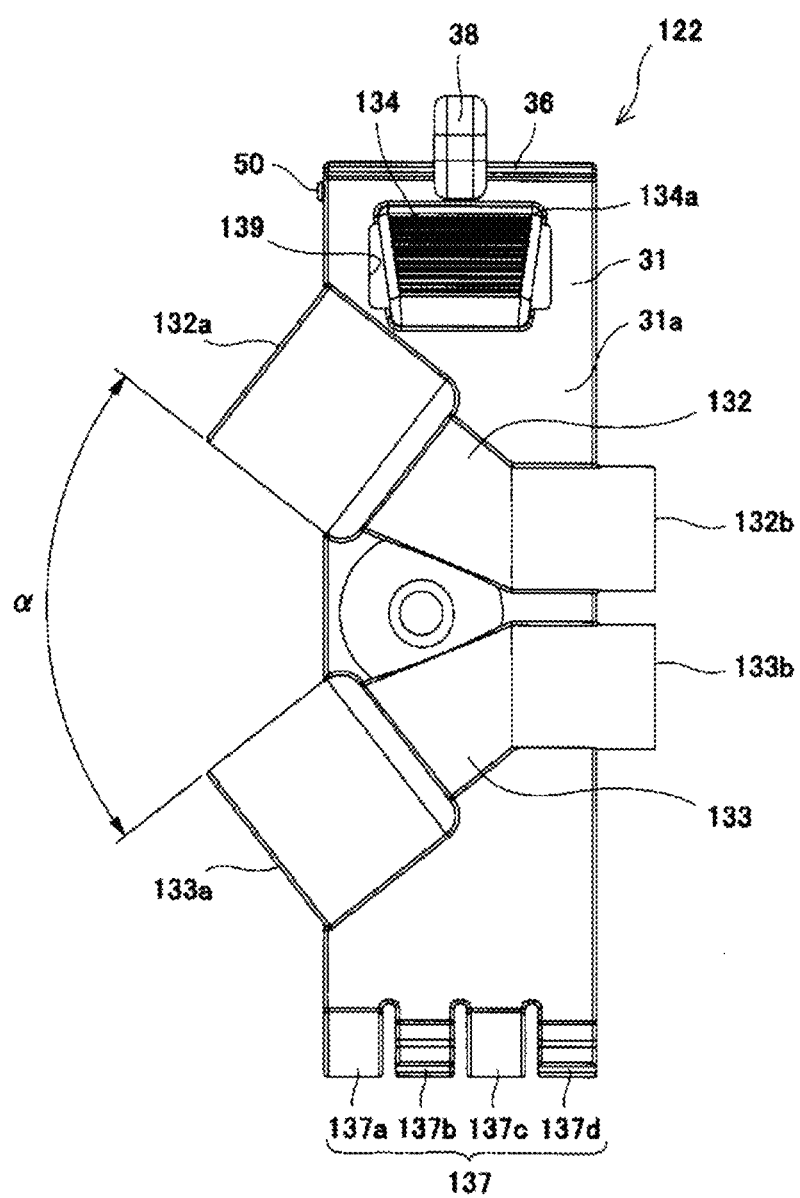

The flexibility of the connector portions 132 and 133 is lower than the flexibility of the plate-shaped holder body 31. In such a situation, as described above, by making the angle α larger than that in the first embodiment, the connection area (contact area) of the connector portions 132 and 133 with respect to the holder body 31 increases, and the flexibility of the holder body 31 in the length direction (the vertical direction in the drawing of FIG. 8(b) is further impaired due to the presence of the connector portions 132 and 133. Since the holder 122 is attached to the housing 11 while being bent, the workability deteriorates when the flexibility of the holder body 31 decreases. Thus, in the present embodiment, a window 139 is provided in which the opening of the window (weak portion) 39 provided for the purpose of adjusting the flexibility of the holder body 31 in the first embodiment is made larger. Thereby, the flexibility of the holder body 31 can be maintained, and a decrease in workability when setting the holder 122 on the housing 11 can be suppressed. With the window 139 having a large opening, a pushing portion 134 having a placement face 134a larger than the placement face 34a of the pushing portion 34 of the first embodiment is employed to cover this window 139.

In the present embodiment, with the discharge tube 3 attached to the discharge port 132b and the supply tube 2 attached to the supply port 133b as shown in FIG. 10, the supply tube 2 and the discharge tube 3 intersect with each other. In many cases, a tube set 110 in which the supply tube 2 and the discharge tube 3 are each wound in such a state, and the pump tube 21, the holder 122, the supply tube 2 and the discharge tube 3 are integrally assembled is packed in a bag and stored until use.

By intersecting the supply tube 2 and the discharge tube 3 with each other in this way, the tube set 110 can be stored compactly, and the curvature of each of the supply tube 2 and the discharge tube 3 can be made small compared with the case where these tubes are wound without the supply tube 2 and the discharge tube 3 intersecting with each other, so that the stress acting on these tubes can be reduced, and deterioration of the tubes can be suppressed.

Further, in the present embodiment, as shown in FIG. 10, a projection 50 is provided on the upper side face of the holder 122. The projection 50 can be formed in a columnar or spherical shape, for example. There may be a slight clearance between the holder 122 and the wall forming the installation space of the holder 122 in the housing 11. Therefore, when the rotor body 42 (see FIG. 1) rotates, the upper portion of the holder 122 may move left and right, and a slight squeak noise may occur. Therefore, the provision of the projection 50 can eliminate the clearance and reduce squeak noise. In addition, by making the projection 50 spherical, it is possible to prevent increase in the feeling of resistance when the holder 122 is installed in the housing 11.

Further, in the present embodiment, a second engagement portion 137 obtained by modifying the second engagement portion 37 in the first embodiment as follows is used.

As shown in FIG. 7, the second engagement portion 137 has one engagement portion 137a and three claw-shaped portions 137b to 137d which are different from the four claw-shaped portions 37a to 37d in the first embodiment. The engagement portion 137a and the claw-shaped portions 137b to 137d are disposed side by side at intervals in the short-side direction (the left-right direction) at the other end (lower end) of the holder body 31 in the longitudinal direction. Specifically, the engagement portion 137a extends downward, and has a distal end formed in a columnar shape. The engagement portion 137a protrudes in one thickness direction and the other thickness direction of the holder body 31. The claw-shaped portions 137b to 137d also extend downward, and have the distal ends formed in a substantially semi-cylindrical shape in side view. The distal ends of the claw-shaped portions 137b to 137d alternately protrude in any of one thickness direction and the other thickness direction of the holder body 31. Specifically, the outer peripheral curved face portion of the claw-shaped portion 137b is disposed on the back face 31b side of the holder body 31, the outer peripheral curved face portion of the claw-shaped portion 137c is disposed on the front face 31a side of the holder body 31, and the outer peripheral curved face portion of the claw-shaped portion 137d is disposed on the back face 31b side of the holder body 31. Note that the axis of the engagement portion 137a and each axis of the claw-shaped portions 137b to 137d substantially coincide with each other.

Figure 12A:
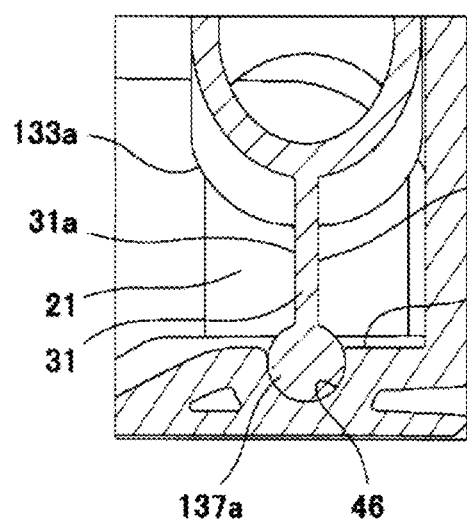
FIG. 12(*a*) is a sectional view taken along line XIIa-XIIa of FIG. 11, and FIG. 12(*b*) is a sectional view taken along line XIIb-XIIb of FIG. 11.

On the other hand, as shown in FIG. 12(a) in the second embodiment, similarly to the first embodiment, a portion (bank portion) 11e is formed below the inner peripheral face 11b of the housing 11, and the second engagement groove 46 extending in the left-right direction is formed in this portion 11e. The second engagement groove 46 is formed to be a substantially semicircular recess in side view. That is, as shown in FIG. 12(a), in a state where the engagement portion 137a is fitted into the second engagement groove 46, a portion of the outer peripheral curved face of the engagement portion 137a does not come into contact with the second engagement groove 46.

Figure 12B:
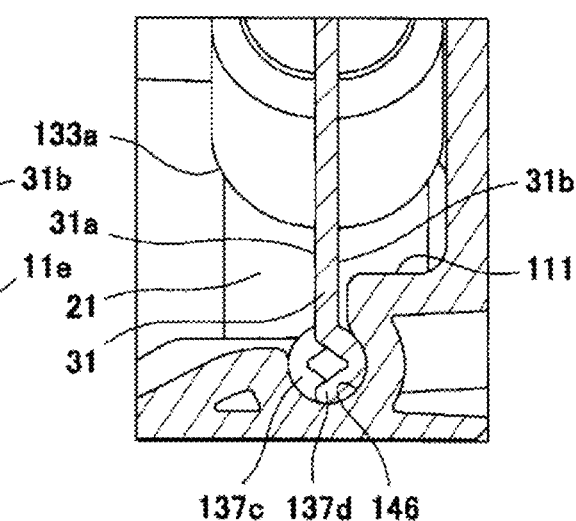

As shown in FIG. 12(b), a high bank portion 111 having an upper face higher than the portion 11e is formed on a side (right side) of the portion 11e on the inner peripheral face 11b of the housing 11 (FIG. 6). The thick wall portion of the high bank portion 111 has a third engagement groove 146 which is formed continuously with the second engagement groove 46 and into which the engagement portion 137d is fitted. The third engagement groove 146 is formed to be a substantially ¾ circular recess in side view. As a result, as shown in FIG. 12(*b*), in a state where the engagement portion 137*d* is fitted into the third engagement groove 146, most of the outer peripheral curved face of the engagement portion 137*d* disposed on the back face 31*b* side of the holder body 31 is in contact with the third engagement groove 146.

Here, as described above, when the curvature of the curved portion of the pump tube 21 is reduced (the radius of curvature is increased), the reaction force from this inner peripheral face 11*b* easily acts on the pump tube 21 that contacts the inner peripheral face 11*b* of the housing 11, so that there is a possibility that the pump tube 21 will move toward the front from the set position due to the reaction force. Along with this, the holder is displaced so that its upper part is released and inclined forward. When the holder is automatically ejected, the holder is displaced so that its upper part is released and inclined forward. In these cases, when the second engagement portion of the holder is not securely engaged with the second engagement groove, the holder may be displaced forward and sideward, or the second engagement portion may come off the second engagement groove.

Therefore, by configuring the second engagement portion 137 as described above, even in the state in which the holder 122 is in the forwardly inclined posture toward the front, that is, the engagement portion 137*a* of FIG. 12(*a*) rotates counterclockwise on the drawing of FIG. 12(*a*), and the claw-shaped portion 137*d* of FIG. 12(*b*) rotates counterclockwise on the drawing of FIG. 12(*b*), the outer peripheral curved face of the engagement portion 137*a* disposed on the left end of the holder 122 can maintain the state of coming into contact with the inner peripheral wall of the second engagement groove 46, and the outer peripheral curved face of the claw-shaped portion 137*d* disposed at the right end of the holder 122 can maintain the state of coming into contact with the inner peripheral wall of the third engagement groove 146. That is, even when the holder 122 is in the forwardly inclined posture, the engagement with the grooves of the holder 122 at both left and right end portions can be maintained. Accordingly, it is possible to prevent the holder 122 from being displaced toward the front and the side, and the second engagement portion 137 from coming off the second engagement groove 46 or the third engagement portion 146.

Also, as shown in FIG. 4 of the first embodiment, an inner peripheral face of one end of the supply tube 2 and an inner peripheral face of one end of the discharge tube 3 are connected to connection flow paths 22*a* and 22*b* located in the holder 22, and the connection flow paths 22*a* and 22*b* have curved faces that are tangent to the blood flow. In a sectional view, the arc portions of the curved face are provided so as to face each other. With such a configuration, hemolysis of blood can be prevented as compared with the case where the connection flow paths 22*a* and 22*b* are not curved. It should be noted that the configuration of FIG. 9 of the second embodiment can be similarly configured.

Further, in FIG. 4 of the first embodiment, the inner peripheral face at the downstream end of the supply tube 2 and the inner peripheral face at the upstream end of the discharge tube 3 may be connected to the curved face without any step. With this configuration, hemolysis of blood can be further prevented. It should be noted that the configuration of FIG. 9 of the second embodiment can be similarly configured.

<Other Configurations>

Although the holder 22 is formed in a substantial shape in the tube set 10 of the present embodiment, the present invention is not limited to such a shape but may be a roughly square or roughly polygonal shape, and it is also possible to use a partially curved shape. That is, the holder 22 may have any shape as long as the holder body 31 and the connector portions 32 and 33 are integrally formed. Further, the shapes of the engagement portions 36 and 37 of the holder 22 are not limited to the shapes described above, but may be disposed upside down. The engagement portions 36 and 37 are provided at both ends of the holder body 31 in the longitudinal direction, but may not be provided at both ends in the longitudinal direction as long as they are formed in the holder body 31 so as to be located apart from each other in the longitudinal direction. For example, the engagement portions 36 and 37 may be formed so as to protrude from the back face 31*b* of the holder body 31.

In the tube set 10 of the present embodiment, the window 39 is formed as a weak portion of the holder 22, but the present invention is not limited to the window 39. For example, a recess may be formed in the vicinity of the first engagement portion 36, or the thickness in the vicinity thereof may be reduced. In addition, two-color molding may be performed so as to be easily bent partially, and a plurality of windows may be formed. Further, first, the first engagement portion 36 may be attached to the housing, and then the second engagement portion 37 may be attached to the housing.

In the tube pump 1 of the present embodiment, the supply tube 2 is disposed on the upper side, and the discharge tube 3 is disposed on the lower side, but the two tubes 2 and 3 may be disposed upside down. In this case, the roller 43 rotates clockwise, whereby the liquid in the pump tube 21 is fed clockwise.

REFERENCE CHARACTERS LIST

1 tube pump
2 supply tube
3 discharge tube
10 tube set
11 housing
11*b* inner peripheral face
12 rotor
21 pump tube
22, 122 holder
22*a*, 22*b*, 122*a*, 122*b* connection flow path
31 holder body
32, 132 supply side connector portion
33, 133 discharge side connector portion
34 pushing portion
34*a* placement face
36 first engagement portion
37 second engagement portion
39, 139 window (weak portion)
45 first engagement groove
46 second engagement groove
132*a* insertion port (first insertion port)
132*b* discharge port
133*a* insertion port (second insertion port)
133*b* supply port

The invention claimed is:

1. A holder for attaching tubes to a housing of a tube pump, the tubes including a pump tube, a supply tube for supplying a liquid to the pump tube, and a discharge tube for discharging the liquid from the pump tube, the holder comprising:
 a plate-shaped holder body extending in a first direction that is a longitudinal direction of the holder body;
 a pair of connector portions located on the holder body and arranged in the longitudinal direction to support two ends of the pump tube;
 a first engagement portion located at one of the longitudinal ends of the holder body in the longitudinal direction to engage with a first engagement groove of the housing; and
 a second engagement portion located at the other of the longitudinal ends of the holder body in the longitudinal direction to engage with a second engagement groove of the housing, wherein
 the first engagement portion protrudes from a front face of the holder body in a thickness direction of the holder body,
 the second engagement portion includes a plurality of elastically deformable engagers arranged in a width direction of the holder body, the width direction crossing both the longitudinal direction and the thickness direction,
 the plurality of engagers include alternating first and second engagers each of which has a curved outer face bulging in the thickness direction, and
 the curved outer face of the first engager and the curved outer face of the second engager face away from each other in the thickness direction.

2. The holder according to claim 1, further comprising a slit formed between adjacent engagers of the plurality of engagers of the second engagement portion.

3. The holder according to claim 2, wherein the slit is longer than the curved outer face of each of the plurality of engagers in the longitudinal direction.

4. The holder according to claim 1, further comprising a guide protrusion located at the one of the longitudinal ends of the holder body, extending over a part of the holder body in the width direction, and protruding from the one of the longitudinal ends in the longitudinal direction to engage with a guide groove of the housing.

5. The holder according to claim 1, further comprising a pushing portion located on the holder body and between the first engagement portion and the pair of connector portions, the pushing portion protruding from the front face of the holder body in the thickness direction.

6. The holder according to claim 5, wherein
 the pushing portion includes an outer face facing in the thickness direction and extending in the longitudinal direction, and
 the outer face of the pushing portion is inclined away from the front face of the holder body toward the other of the longitudinal ends of the holder body.

* * * * *